United States Patent
Brookbank

(10) Patent No.: US 8,708,664 B2
(45) Date of Patent: Apr. 29, 2014

(54) SYSTEM TO MEASURE VIBRATIONS USING FIBER OPTIC SENSORS

(75) Inventor: Earl B. Brookbank, Claremore, OK (US)

(73) Assignee: Baker Hughes Incorporated, Houston, TX (US)

( * ) Notice: Subject to any disclaimer, the term of this patent is extended or adjusted under 35 U.S.C. 154(b) by 735 days.

(21) Appl. No.: 12/828,662

(22) Filed: Jul. 1, 2010

(65) Prior Publication Data

US 2011/0002795 A1    Jan. 6, 2011

Related U.S. Application Data

(60) Provisional application No. 61/222,268, filed on Jul. 1, 2009.

(51) Int. Cl.
*F04B 49/00* (2006.01)

(52) U.S. Cl.
USPC .................. 417/63; 310/87; 385/98; 385/101

(58) Field of Classification Search
USPC .............. 417/63; 310/71, 87; 385/97, 98, 101
See application file for complete search history.

(56) References Cited

U.S. PATENT DOCUMENTS

| | | | |
|---|---|---|---|
| 5,649,035 A | 7/1997 | Zimmerman | |
| 5,892,860 A * | 4/1999 | Maron et al. | 385/12 |
| 6,888,124 B1 | 5/2005 | Smith | |
| 7,113,660 B2 * | 9/2006 | Andrews et al. | 385/13 |
| 7,208,855 B1 * | 4/2007 | Floyd | 310/71 |
| 7,397,976 B2 | 7/2008 | Mendez | |

* cited by examiner

*Primary Examiner* — Charles Freay
*Assistant Examiner* — Patrick Hamo
(74) *Attorney, Agent, or Firm* — Bracewell & Giuliani LLP

(57) ABSTRACT

A vibration monitoring system for an electrical submersible pump (ESP) that includes a fiber optic cable coupled with the ESP and an optical sensor coupled with the fiber optic cable. The optical sensor emits electromagnetic radiation into the fiber optic cable, some of which reflects back from optical discontinuities provided in the fiber optic cable. By receiving the reflected electromagnetic radiation, the optical sensor estimates the location of the optical discontinuities. Displacement and rate of displacement of the optical discontinuities can be estimated when the reflections are received over a period of time. Because the fiber optic cable, and the optical discontinuities, move with the ESP, displacement measurements of the optical discontinuities correlate to ESP movement, including ESP vibration.

19 Claims, 7 Drawing Sheets

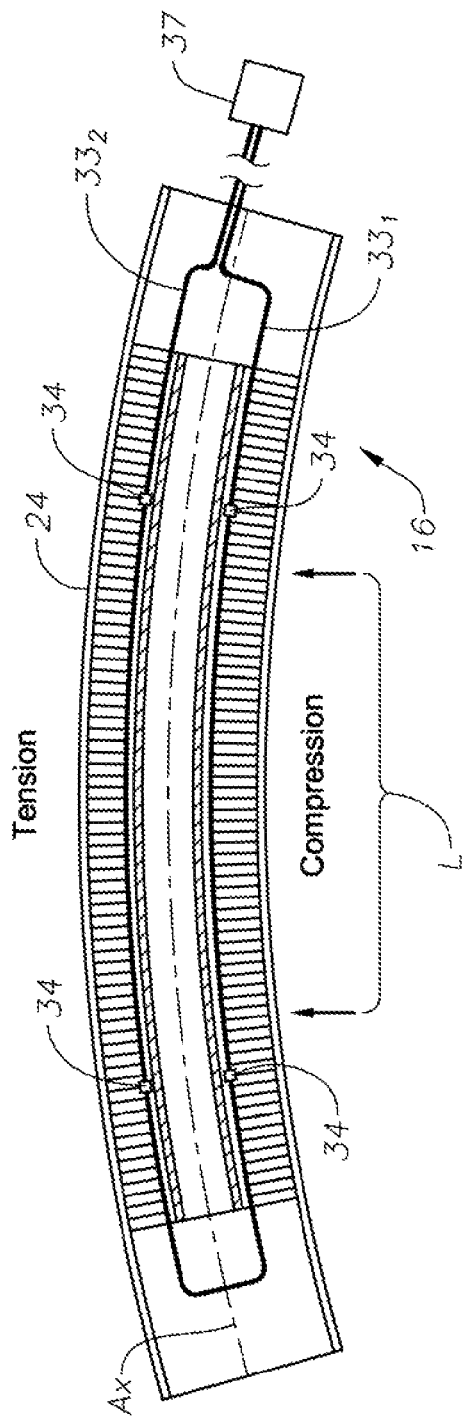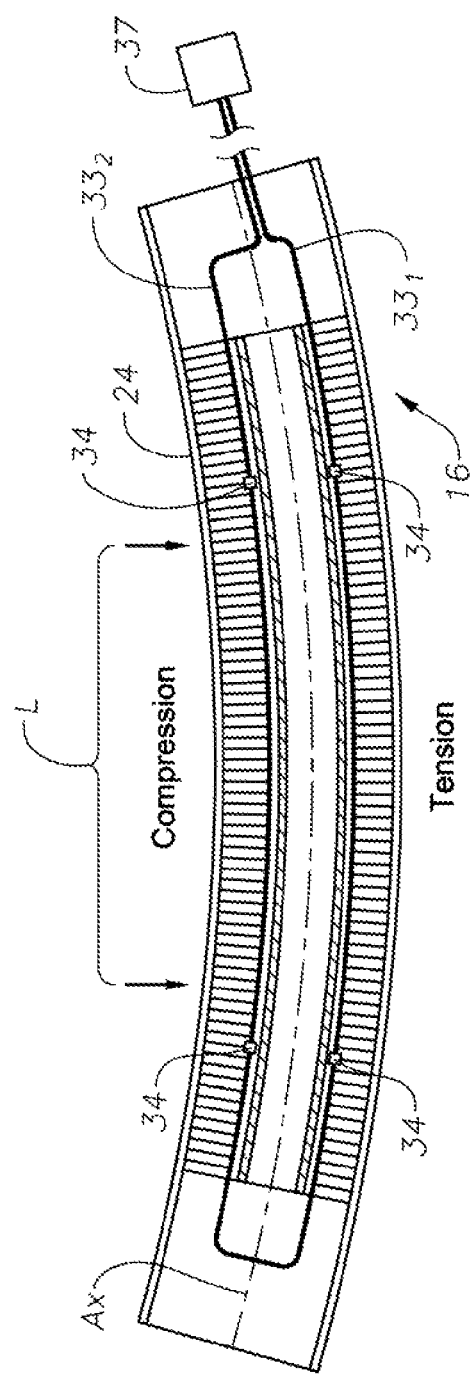

SYSTEM TO MEASURE VIBRATIONS USING FIBER OPTIC SENSORS

CROSS REFERENCE TO RELATED APPLICATIONS

This application claims priority to and the benefit of U.S. Provisional Application No. 61/222,268 filed Jul. 1, 2009, the full disclosure of which is hereby incorporated by reference herein.

BACKGROUND

1. Field of Invention

The present invention relates to fiber optic sensors, and in particular, to a system using fiber optic sensors to measure vibration in downhole electric submersible pump systems.

2. Description of Related Art

Electrical submersible pump (ESP) systems may be deployed within a wellbore to pump downhole fluid to the surface. An ESP system may typically include an electric motor and a pump that is used to pump oil or other fluids within a wellbore. The electric motors have a rotatable rotor that is contained within a stationary stator. During operation in a wellbore, ESP systems may vibrate for multiple reasons. For example, when fluid film bearings are used to protect between a rotor shaft and a bearing sleeve, the bearings may become destabilized due to lack of an applied side load to cause excessive motor vibration. Motor vibration induces the bearings to vibrate, that in turn can cause the bearing sleeve to break through the oil film. When the oil film is breached, metal to metal contact occurs that can lead to premature wear and motor failure. Motor vibration can also occur when unexpectedly high levels of gas are being pumped by the ESP. While vibration monitoring systems may be employed, vibration measurements are typically limited to average overall levels.

SUMMARY OF INVENTION

In an example embodiment, a fiber optic cable or cables may be utilized in conjunction with an electric submersible pump assembly to measure and monitor variables throughout the assembly including vibration and temperature. Fiber optic cables are typically a glass fiber that has been drawn, and then modified at precise locations using a laser or other means, and then enclosed within a sheath. The modifications allow an optical time domain reflectometer to measure reflected laser light from these locations. The time difference between the laser pulse and the reflection is used to determine the location of the modified fiber in the cable. The sheath is typically stainless steel but may be made of other material as well. The fiber optic cable may be installed on the outside of the ESP or built into (installed inside) the ESP components (motor, seal, pump, etc.). By properly placing the fiber optic cables so that axial deflections or strain on opposite sides of the ESP may be measured, lateral bending and vibration may also be measured.

By attaching a fiber optic cable that has been prepared to measure the location of manufactured anomalies in the fiber to a motor, the deflection of an ESP assembly, and as a result, the vibration of the ESP assembly may be measured. Deflections along the length of the fiber optic cable can be measured using optical time domain reflectometery or swept wavelength interferometry techniques.

BRIEF DESCRIPTION OF THE DRAWINGS

FIG. 4 is a longitudinal sectional view of the electric submersible pump of FIG. 2 while undergoing a bending force.

FIG. 5 is a longitudinal sectional view of the electric submersible pump of FIG. 2 while undergoing a bending force in the opposite direction of FIG. 5.

DETAILED DESCRIPTION OF THE INVENTION

Figure 1:
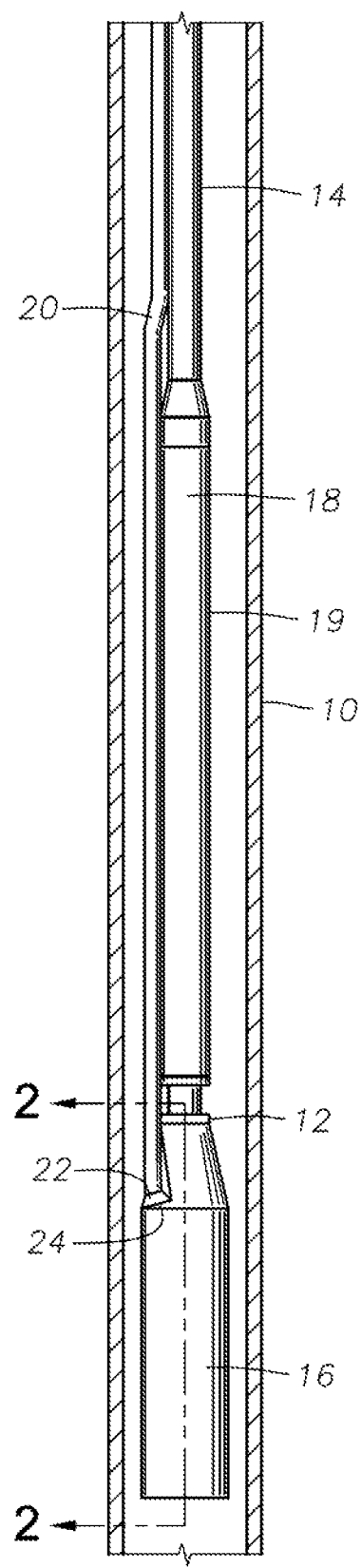
FIG. 1 is an elevational view of a well within which an electric submersible pump is disposed.

FIG. 1 is an elevational section view of a well 10 with an ESP disposed therein, the embodiment of the ESP includes an electric submersible pump 12 mounted to a string of tubing 14. Pump 12 includes an electric motor 16 and a pump section comprising a centrifugal pump assembly 18 within housing 19. A cable 20 extends downhole, terminating in a motor lead to provide power to the electric motor 16. A pothead connector 22 is mounted to the motor lead of cable 20, and electrically connects and secures the motor lead of cable 20 to a housing 24 outside of motor 16. Pump 12 is used to pump well fluids from within the well 10 to the surface.

Figure 2A:
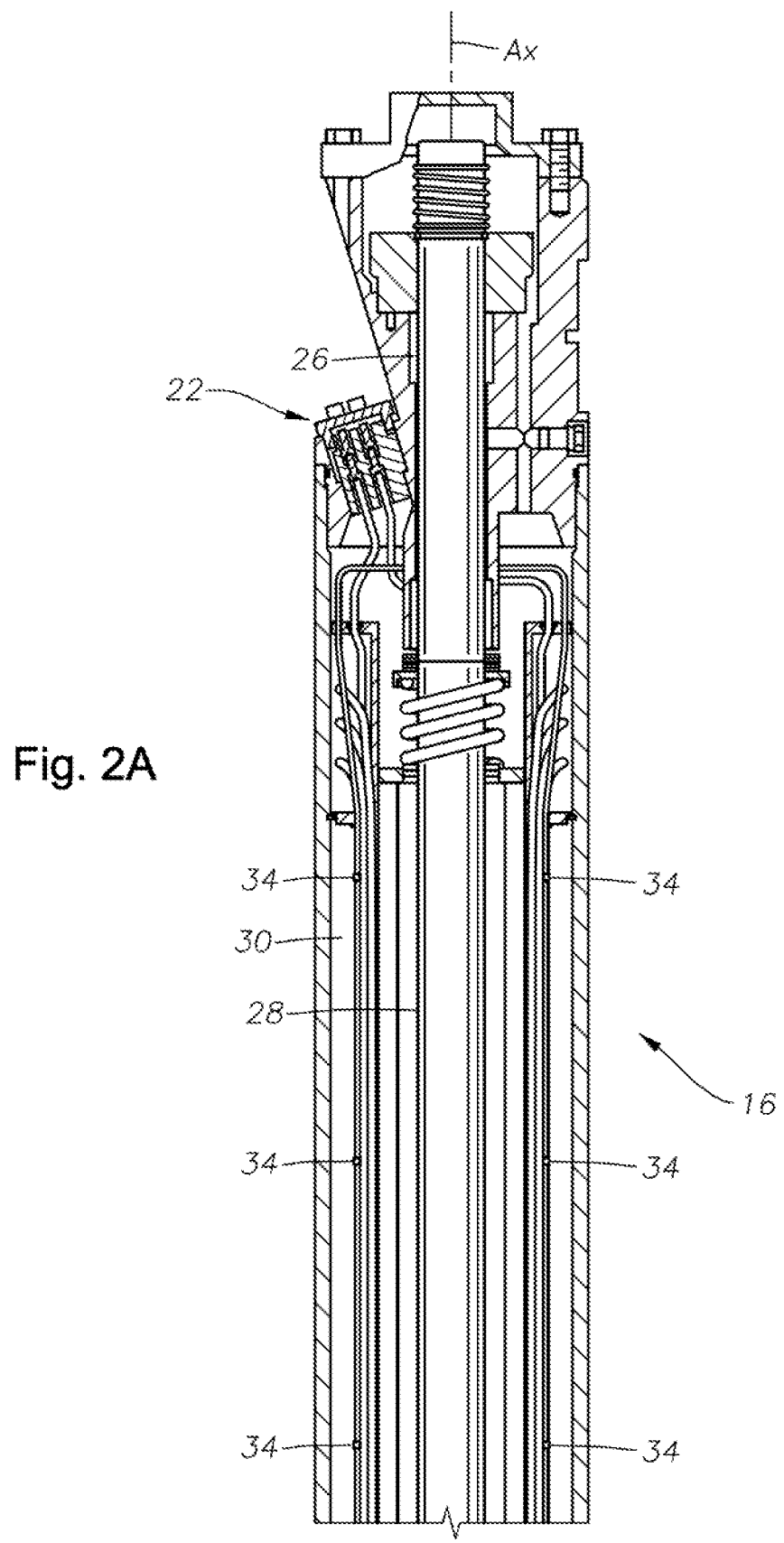
FIG. 2A is a longitudinal sectional view of the upper portion of the electric submersible pump of the present invention taken along the line 2-2 of FIG. 1.
Figure 2B:
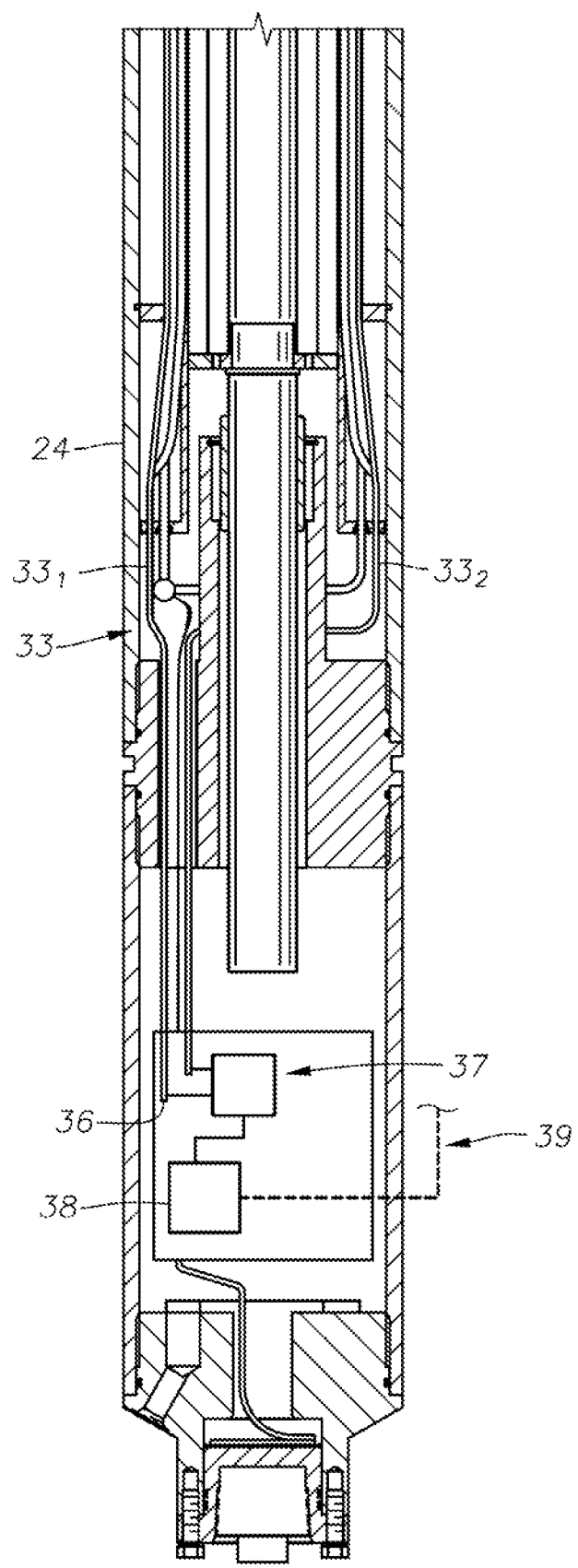
FIG. 2B is a longitudinal sectional view of the lower portion of the electric submersible pump of the present invention taken along the line 2-2 of FIG. 1.

Shown in FIG. 2 is a side sectional view of an example embodiment of the motor 16 taken along lines 2-2 of FIG. 1. As seen in FIG. 2, the housing 24 surrounds the components within motor 16 and is sealed to protect components in the motor 16 from contact with well fluids. A drive shaft 26 is coupled to a shaft (not shown) within pump 18 (FIG. 1) to transfer torque from motor 16 to pump 18. Motor 16 creates a torque on shaft 26 to cause the shafts to rotate, providing power to drive pump 18. In the example embodiment of FIG. 2, motor shaft 26 is cylindrical and extends coaxially through the motor 16. A rotor 28 is shown mounted around the shaft 26 for rotation within a stationary stator 30. Rotor 28 is comprised of a number of laminated disk-like plates (not shown) coaxially stacked along a portion of the shaft 26. Stator 30 is an annular member anchored along a portion of an inner surface of the housing 24 and circumscribing the rotor 28. An annular space separates the rotor 28 and stator 30.

Still referring to FIG. 2, a fiber optic cable 33 is shown included with the example embodiment of the motor 16. In an example embodiment, the fiber optic cable 33 is made up of a drawn glass fiber and encased in a sheath; an example of sheath material is a substantially rigid material such as stainless steel or other suitable material. In the example embodiment of FIG. 2, the fiber optic cable 33 includes optical discontinuities 34 at discrete locations along the length of the fiber optic cable 33. The optical discontinuities 34 may include locations where the index of refraction changes in the fiber optic cable 33. Optionally, the optical discontinuities 34 may be formed in the fiber optic cable 33 such as by applying a laser beam to the fiber optic cable 33. In another example embodiment, the optical discontinuities 34 include connection points, such as a splice or a cable connector. The fiber optic cable 33 is shown axially passing through the stator 30 at an angular position with respect to an axis $A_X$, exiting an end of the stator 30 proximate the pothead connector 22, looping to another angular position of the stator 30, and passing back axially through the stator 30. Looping back through the stator 30 defines a pair of legs $33_1$, $33_2$ in the fiber optic cable 33. The legs $33_1$, $33_2$ of FIG. 2 exit the stator 30 at the end distal from the pothead connector 22 and connect to a fiber optic termination point 36 shown provided in the housing beneath a lower end of the shaft 26.

In an example embodiment, the termination point 36 may include sensors, such as for measuring conditions at the pump 16, such as temperature, pressure, vibration, and the like. As shown in FIG. 2, an optical time-domain reflectometer (OTDR) 37 may be included with the termination point 36 or be located on the surface using a fiber optic cable to transmit the signals between the ESP and the OTDR 37. An OTDR 37 can send optical pulses into an optical fiber and collect electromagnetic radiation, such as visible light, that is scattered or otherwise reflected from within the optical fiber. Changes in an index of refraction in the optical fiber can define scatter or reflection points. Analyzing the collected return light can yield the distance to the changes in the index of refraction. Thus, in an example embodiment, the OTDR 37 can be used to monitor the relative location(s) of the optical discontinuities 34.

The termination point 36 may optionally include a processor 38 integrated or otherwise in communication with the OTDR 37. The processor 38 can include signal processing software for generating a signal or data representative of the measured conditions. A communication link 39 can provide means to transmit the generated signal or data from the processor 38 back to the surface. The communication link 39 be hard wired, fiber optic cable, telemetry, or other transmission means.

Figure 3:
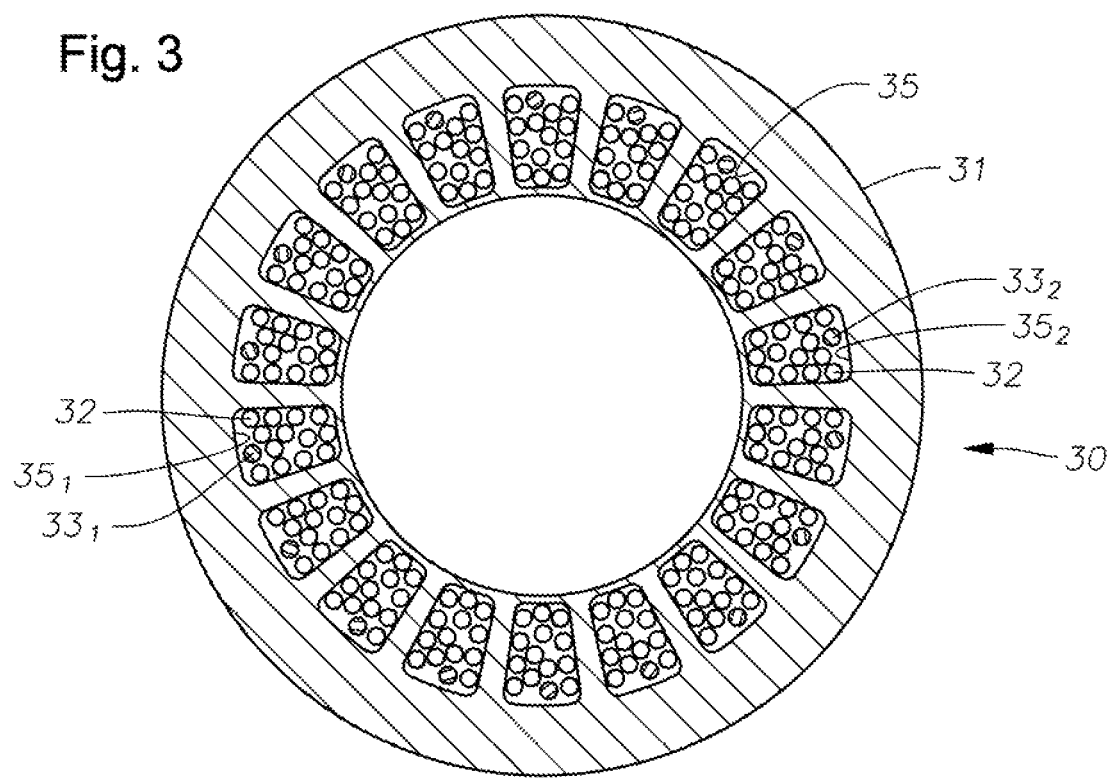
FIG. 3 is a horizontal sectional view of the electric submersible pump of FIG. 2.

Referring now to FIG. 3, a sectional view is provided of a section of a stator 30 and illustrating a lamination 31 in a plan view. Coaxially stacking the laminations 31 form the stator 30. Formed axially through each lamination 31 are slots 35; so that when the slots 35 are aligned, a passage extends axially through the stator 30. In the example embodiment of FIG. 3, the slots 35 are arranged along an inner diameter of the stator 31. Wire like electrical conductors 32 are shown inserted through the aligned slots 35 and extend along the length of the stator 30. The conductors 32 form a winding through the slots 35 either by looping from one slot 35 to another, or by having ends that are connected to ends of other conductors 32 in other slots 35.

In the example embodiment of FIG. 3, the fiber optic cable 33 is shown inserted within slots $35_1$, $35_2$ that are disposed on substantially opposing sides of the lamination 31. In an example, one leg $33_1$ of the fiber optic cable 33 travels through a passage aligned with slot $35_1$, i.e. one side of the motor 16; loops to the passage aligned with slot $35_2$, then travels through the passage (leg $33_2$) and into slot $35_2$. This arrangement forms the two legs $33_1$, $33_2$ of the fiber optic cable 33; that while in the stator 30 are parallel to one another (FIG. 2).

FIG. 4 schematically represents an embodiment of the motor 16 bending or otherwise deforming in response to an applied side load L. In the example of FIG. 4, the load L compresses a portion of the motor 16 on one side of the axis $A_X$ and tensions a portion of the motor 16 on the other side of the axis $A_X$. In FIG. 5 a load L is applied to an opposite side of the motor 16 to reverse the sides of the motor 16 in compression and tension. Thus in the example of FIG. 4 leg $33_1$ is in compression and leg $33_2$ is in tension, whereas in the example of FIG. 5 leg $33_1$ is in tension and leg $33_2$ is in compression. The legs $33_1$, $33_2$ elongate when in tension and shorten when in compression, thereby axially moving the optical discontinuities 34 with respect to the OTDR 37. Accordingly, the amount of deflection or deformation in the legs $33_1$, $33_2$ can be measured by activating the OTDR 37 and analyzing the relative distance shift(s) of the optical discontinuities 34. For the purposes of discussion herein, deflection of the legs $33_1$, $33_2$ includes lateral (radial) as well as axial deformation.

Monitoring displacements of the optical discontinuities 34 with the OTDR 37 can be correlated to time span and time frequency to indicate when the displacements constitute vibratory motion and the vibration mode. The vibratory motion can include lateral vibrations in the motor 16 or a specific portion of the motor 16. Moreover, the vibratory motion can include lateral deflection of the motor 16 oscillating between the configurations of FIG. 4 and FIG. 5, wherein the deformation can be compression or tension. The OTDR 37 can communicate signals to the processor 38 representative of the vibrations monitored by the OTDR 37. The processor 38 can in turn process the monitored vibrations into quantified values that can be used for analysis. The quantified values can be conveyed to the surface via the communication link 39. Optionally, the processor 38 can be disposed at the surface and receive signals directly from the OTDR 37.

In an alternate embodiment, the temperature of the motor 16 may be measured and monitored by communicating a temperature sensor to the fiber optic cable 33. In an alternate embodiment, multiple fiber optic cables 33 may be installed inside the slots 35 and would allow for vibration to be measured in multiple planes.

Another method of measuring vibration is to measure the strain from deformations during vibratory oscillation. Strain measurements may be taken along a deforming surface and along a path oblique or normal to a path of vibratory oscillation. A fiber optic sensor, such as a Fabry-Perot interferometer acoustic emissions sensor, may be employed. The Fabry-Perot interferometer acoustic emissions sensor has a high sensitivity to detect low levels of strain caused by vibration. The signal from the fiber optic sensor may be transmitted to the surface using a fiber optic wire, and analyzed in the same manner using a fast Fourier transform or other data reduction technique that is presently being used.

Figure 6:
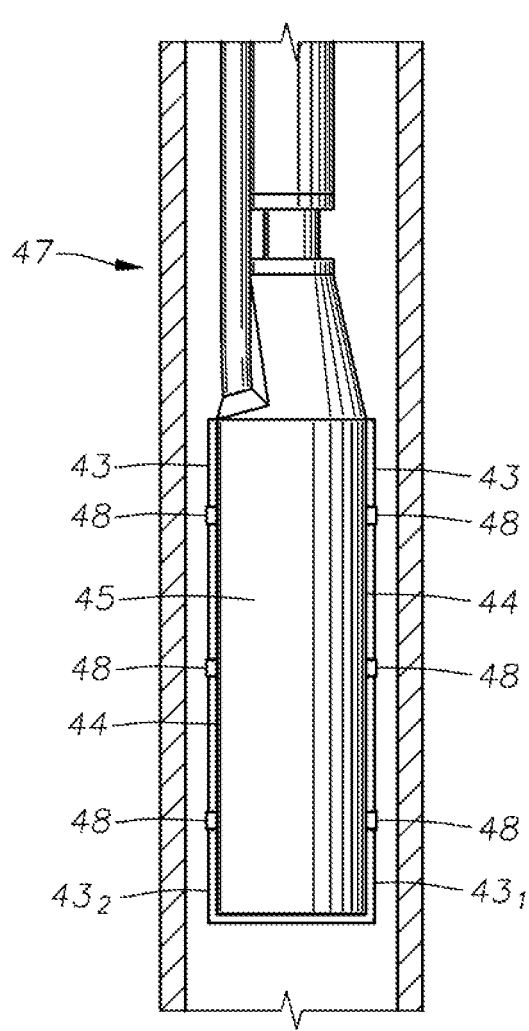
FIG. 6 is an elevational view of a motor portion of an alternate embodiment electric submersible pump.

In an oscillatory vibration, the motor 16 may vibrate similar to a rod or guitar string thereby producing nodes (no lateral oscillation) separated by portions of the motor 16 that are oscillating and defining an anti-node at the location of maximum lateral deflection. As illustrated in FIG. 6, in an additional alternate embodiment, a fiber optic cable 43 is shown coupled to an exterior of a housing 44 of a motor portion 45 of an ESP assembly 47. Optical discontinuities 48 are illustrated in the fiber optic cable 43, and are optionally set a known discrete locations. The fiber optic cable 43 may be housed in a sheath (not shown) that is rigidly attached to the ESP assembly 47 so that a deflection (stretching or compression) of the ESP assembly 47 where it couples with the fiber optic cable 43 will correspondingly deflect the fiber optic cable 43. As discussed above, monitoring relative motion of the optical discontinuities 48 with respect to an optical sensor, such as an OTDR, can yield information regarding vibration of the ESP assembly 47. In this example embodiment, legs $43_1$, $43_2$ of the fiber optic cable 43 are disposed from one another at substantially opposite sides of the housing 44. Optionally, an additional fiber optic cable (not shown) with legs disposed at substantially opposite locations around the ESP assembly 47 can be provided and offset from the fiber optic cable 43 by an angular amount.

Figure 8:
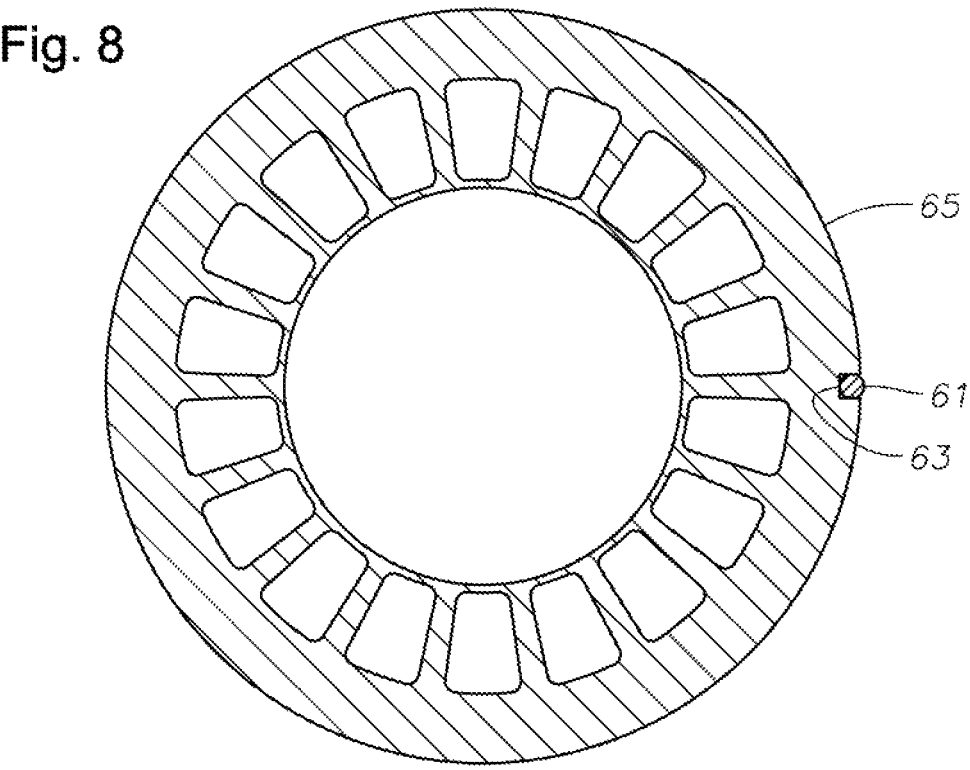
FIG. 8 is sectional view of a stator of an alternate embodiment electric submersible pump.
Figure 7:
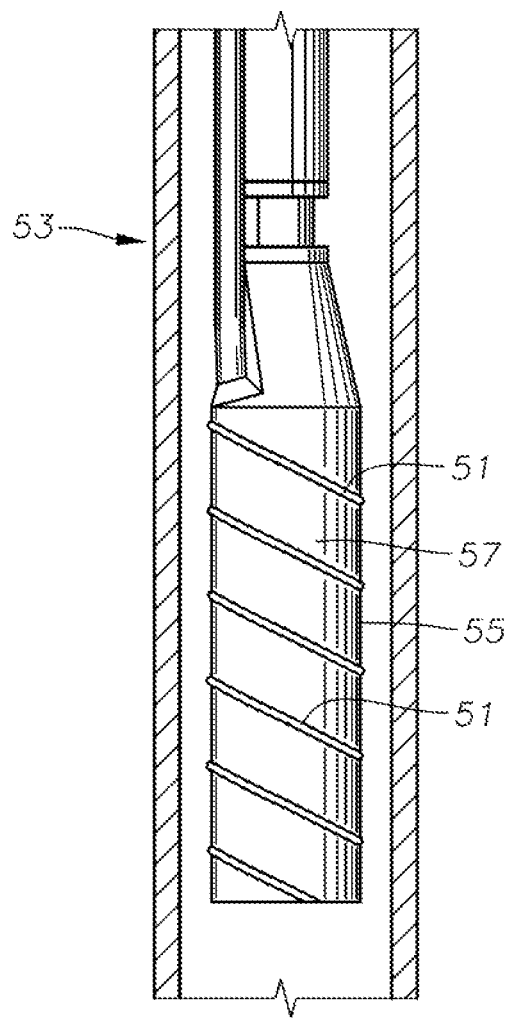
FIG. 7 is an elevational view of a motor portion of an alternate embodiment electric submersible pump.

Illustrated in FIG. 7 is yet another alternate embodiment, depicting a fiber optic cable 51 shaped into a helix that spirals around a portion of an ESP assembly 53. In this particular alternate embodiment, the fiber optic cable 51 is spiraled around the exterior of housing 55 of the motor portion 57 of ESP assembly 53. Referring to FIG. 8, in an additional alternate embodiment, a fiber optic cable 61 is run through a slot 63 in an outer periphery of a stator lamination 65 as found within a motor portion of an ESP assembly. Thus, forming a stack of laminations 65 and aligning the slot 63 forms a stator with an elongated groove in which the fiber optic cable 61 can be disposed. In an alternate embodiment, the fiber optic cable 61 may also be rigidly connected to the interior surface of the motor housing 24.

Figure 9:
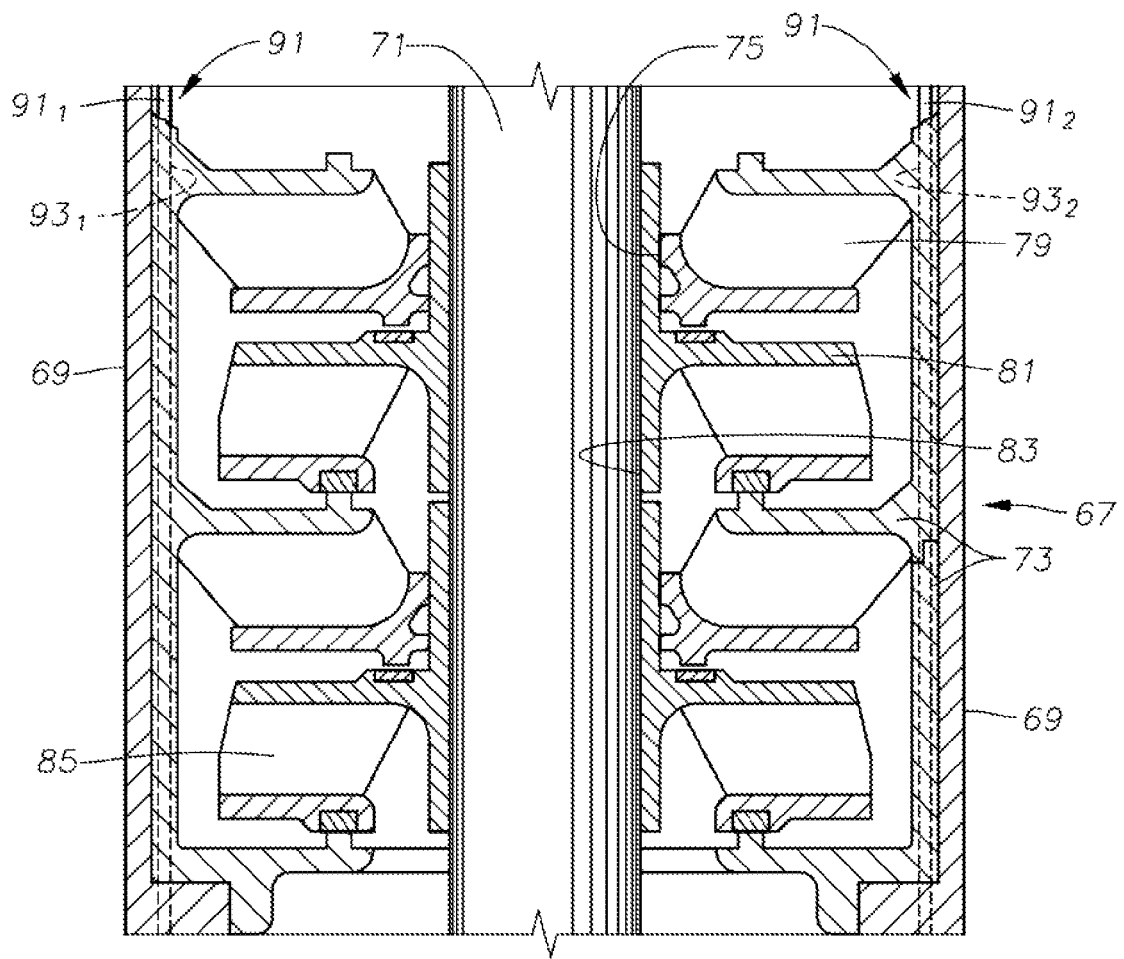
FIG. 9 is a longitudinal sectional view of a pump portion of an alternate embodiment electric submersible pump.

In additional alternate embodiments, slots could also be placed in various elements of an ESP assembly. For example, in a particular alternate embodiment illustrated in FIG. 9, a centrifugal pump 67 has a housing 69 that protects many of the pump 67 components. Pump 67 contains a shaft 71 that extends longitudinally through the pump 67. Diffusers 73 have an inner portion with a bore 75 through which shaft 71 extends. Each diffuser 73 contains a plurality of passages 79 that extend through the diffuser 73. Each passage 79 is defined by vanes (not shown) that extend helically outward from a central area. Diffuser 73 is a radial flow type, with passages 79 extending in a radial plane. An impeller 81 is placed within each diffuser 73. Impeller 81 also includes a bore 83 that extends the length of impeller 81 for rotation relative to diffuser 73 and is engaged with shaft 71. Impeller 81 also contains passages 85 that correspond to the openings in the diffuser 73. Passages 85 are defined by vanes (not shown). Washers are placed between the upper and lower portions between the impeller 81 and diffuser 73.

Impellers 81 rotate with shaft 71, which increases the velocity of the fluid being pumped as the fluid is discharged radially outward through passages 85. The fluid flows inward through passages 79 of diffuser 73 and returns to the intake of the next stage impeller 81, which increases the fluid pressure. Increasing the number of stages by adding more impellers 81 and diffusers 73 can increase the pressure of the fluid. In order to monitor the stress and strain in the pump 67, legs $91_1$, $91_2$ of a fiber optic cable 91 may be run through corresponding passages $93_1$, $93_2$ located in the outer peripheries of the pump diffusers 73. The legs $91_1$, $91_2$ are run through passages $93_1$, $93_2$ shown disposed at substantially opposite sides of the pump 67.

The invention has significant advantages. Fiber optic cables are utilized in an electric submersible pump assembly to measure and monitor variables throughout the assembly including vibration and temperature. Properly placed fiber optic cables permit axial deflections on opposite sides of the ESP to be measured, thereby enabling lateral bending and vibration to also be measured. In addition, the requirement for downhole electronics may be eliminated by using a fiber optic cable to return measurements to the surface for processing.

While the invention has been shown in only one of its forms, it should be apparent to those skilled in the art that it is not so limited but is susceptible to various changes without departing from the scope of the invention. For example, a fiber optic cable may be placed on the interior or exterior of a desired component of an ESP assembly. In an example embodiment, fiber optic cable can be rigidly attached to a component by soldering, brazing, gluing, combinations thereof, and other like techniques. In an example embodi-ment, distributed temperature and displacement sensing using optical fibers can include techniques based on Raman, Brillouin, and Rayleigh scattering as well as those involving multiplexed fiber Bragg gratings. The scattering techniques can employ optical time domain reflectometry. Alternatively, the Rayleigh backscatter can be measured using swept wavelength interferometry (SWI) as a function of length in optical fiber with high spatial resolution.

What is claimed is:

1. A method of monitoring an electrical submersible pumping system (ESP) comprising:
   (a) providing a fiber optic cable having optical discontinuities at a spaced apart locations in the fiber optic cable;
   (b) coupling the fiber optic cable with the ESP so that a first portion of the optic cable containing at least one of the optical discontinuities is offset from one side of an axis of the ESP and a second portion of the optic cable containing at least one other of the optical discontinuities is offset from an opposite side of the axis;
   (c) emitting electromagnetic radiation into the fiber optic cable, a portion of which reflects from the optical discontinuities;
   (d) operating the ESP, receiving and analyzing the reflected electromagnetic radiation to determine changes in lengths of the first and second portions; and
   (e) comparing the changes and estimating deformation of the portion of the ESP based on the analyzing of step (d).

2. The method of claim 1, wherein step (b) comprises coupling the fiber optic cable to the ESP along a helical path circumscribing the axis of the ESP.

3. The method of claim 1, wherein the ESP deformation is caused by vibration in the ESP and wherein step (e) further comprises detecting vibration in the ESP.

4. A method of monitoring an electrical submersible pumping system (ESP) comprising:
   (a) providing a fiber optic cable having an optical discontinuity at a location in the fiber optic cable;
   (b) coupling the fiber optic cable with the ESP so that when a portion of the ESP deforms that is immediately adjacent the optical discontinuity, the optical discontinuity moves in response to the ESP deformation;
   (c) emitting electromagnetic radiation into the fiber optic cable, a portion of which reflects from the optical discontinuity;
   (d) receiving and analyzing the reflected electromagnetic radiation;
   (e) estimating deformation of the portion of the ESP based on the analyzing of step (d); wherein
      the optical discontinuity comprises a first optical discontinuity and the fiber optic cable comprises a second optical discontinuity; and
      step (b) comprises coupling the fiber optic cable to the ESP along paths disposed substantially on opposite sides of an axis of the ESP so that the first and second optical discontinuities are disposed on substantially opposite sides of the axis.

5. The method of claim 4, wherein the paths are in an orientation selected from the list consisting of substantially parallel with the axis, on an outer surface of the ESP, on an inner surface of the ESP.

6. The method of claim 5, wherein the paths on an outer surface of the ESP are selected from the list consisting of, along an entire length of the ESP, along a portion of the entire length of the ESP, adjacent a motor section of the ESP, adjacent a pump section of the ESP, adjacent a seal section of the ESP, and combinations thereof.

7. The method of claim 5, wherein the path on an inner surface of the ESP is selected from the list consisting of axially through a passage in a stator that is adjacent an inner circumference of the stator, through a passage in a stator that is adjacent an outer circumference of the stator, through a passage in diffusers in a pump of the ESP, and combinations thereof.

8. The method of claim 7, further comprising adjusting a control of the ESP based on the step of detecting vibration in the ESP.

9. The method of claim 4, wherein step (b) comprises coupling the fiber optic cable to a first lateral side of a motor housing of the ESP, under a bottom side of the motor housing of the ESP, and along a second lateral side of the motor housing of the ESP so that the fiber optic cable forms legs on the outer surface of the motor housing of the ESP that are disposed at substantially opposite locations on the outer surface of the motor housing of the ESP, and using an optical time domain reflectometer to perform the emitting and receiving of steps (c) and (d).

10. An electrical submersible pumping system (ESP) comprising:
   a housing;
   a fiber optic cable coupled along a first portion of the housing on one side of an axis of the housing and a second portion of the housing an opposite side of the axis;
   optical discontinuities in the fiber optic cable spaced art from each other with one of the optical discontinuities in the first portion of the fiber optic cable and another of the optical discontinuities in the fiber optic cable in the second portion of the fiber optic cable; and
   an optical sensor assembly coupled with an end of the fiber optic cable, the optical sensor assembly emitting electromagnetic radiation into the fiber optic cable and receiving reflections of the electromagnetic radiation from the optical discontinuities for estimating deformation of the ESP during operation.

11. An electrical submersible pumping system (ESP) comprising:
   a housing;
   a fiber optic cable coupled along a portion of the housing;
   an optical discontinuity in the fiber optic cable disposed at a designated location in the fiber optic cable;
   an optical sensor assembly coupled with an end of the fiber optic cable for estimating deformation of the ESP based on movement of the optical discontinuity; and
   wherein the optical discontinuity comprises a first optical discontinuity and the fiber optic cable comprises a second optical discontinuity and wherein the fiber optic cable couples to the ESP along paths disposed substantially on opposite sides of an axis of the ESP so that the first and second optical discontinuities are disposed on substantially opposite sides of the axis.

12. The system of claim 11, wherein the paths are in an orientation selected from the list consisting of substantially parallel with the axis, on an outer surface of the ESP, on an inner surface of the ESP.

13. The system of claim 12, wherein the paths on an outer surface of the ESP are selected from the list consisting of, along an entire length of the ESP, along a portion of the entire length of the ESP, adjacent a motor section of the ESP, adjacent a pump section of the ESP, adjacent a seal section of the ESP, and combinations thereof.

14. The system of claim 12, wherein the path on an inner surface of the ESP is selected from the list consisting of axially through a passage in a stator that is adjacent an inner circumference of the stator, through a passage in a stator that is adjacent an outer circumference of the stator, through a passage in diffusers in a pump of the ESP, and combinations thereof.

15. The system of claim 12, wherein the fiber optic cable is coupled to the ESP along a helical path circumscribing an axis of the ESP.

16. The system of claim 11, wherein the optical sensor assembly comprises an optical source and receiver, and a processor in communication with the optical source and receiver for calculating vibrational motion of the ESP based on electromagnetic radiation reflected from the optical discontinuity and received by the optical source and receiver.

17. The system of claim 11, further comprising a controller for adjusting an operation of the ESP based on movement of the optical discontinuity.

18. The system of claim 11, further comprising a motor section, a seal section, and a pump section, wherein the motor section, seal section, and pump section are all disposed within the housing.

19. An electrical submersible pumping system (ESP) comprising:
   a motor section having an axis;
   a fiber optic cable coupled to the motor section that comprises legs that extend along the motor section on opposite lateral sides of the axis and connect on a bottom side of the motor section;
   optical discontinuities in the fiber optic cable disposed at designated locations in each of the legs; and
   an optical sensor assembly coupled with ends of the legs for estimating deformation of the ESP based on movement of the optical discontinuities.

* * * * *